United States Patent [19]
Ichikawa

[11] Patent Number: 5,929,988
[45] Date of Patent: Jul. 27, 1999

[54] PARTICULATE DETECTING SENSOR EMPLOYING PARALLEL LIGHT

[75] Inventor: Nobuyuki Ichikawa, Tokyo, Japan

[73] Assignee: Nohmi Bosai, Ltd., Tokyo, Japan

[21] Appl. No.: 08/607,186

[22] Filed: Feb. 26, 1996

[30] Foreign Application Priority Data

Feb. 27, 1995 [JP] Japan .................................. 7-038604

[51] Int. Cl.⁶ .................................................. G01B 11/00
[52] U.S. Cl. ......................... 356/338; 356/335; 356/339; 356/436; 250/574
[58] Field of Search ...................... 356/338, 340, 356/335–337, 339, 349, 343, 436–440; 340/628, 630, 555; 250/574, 564

[56] References Cited

U.S. PATENT DOCUMENTS

| | | | |
|---|---|---|---|
| 3,659,278 | 4/1972 | Jensen . | |
| 4,168,438 | 9/1979 | Morisue | 356/438 |
| 4,226,533 | 10/1980 | Snowman | 356/338 |
| 4,397,557 | 8/1983 | Herwig et al. | 356/342 |
| 4,906,978 | 3/1990 | Best et al. | 356/439 |
| 5,132,548 | 7/1992 | Borden et al. | 356/336 |
| 5,302,837 | 4/1994 | Sawa et al. | 340/630 |

FOREIGN PATENT DOCUMENTS

| | | |
|---|---|---|
| 0031096 | 7/1981 | European Pat. Off. . |
| 0 463 795 | 1/1992 | European Pat. Off. . |
| 93/08461 | 4/1993 | WIPO . |

*Primary Examiner*—Robert H. Kim
*Attorney, Agent, or Firm*—Wenderoth, Lind & Ponack, L.L.P.

[57] ABSTRACT

Light emitted from a light emitting element is converted into parallel light by a lens, and a light receiving element detects scattered light occurring due to particulate existent in a fan-shaped field pattern spreading along the optical path of the parallel light. Since parallel light is used, stray light can be processed within a limited space. Furthermore, since the scattered light of parallel light which occurs due to the particulate is detected using the fan-shaped field pattern, particulate detection can be performed on volumes of air at a high signal-to-noise ratio.

24 Claims, 6 Drawing Sheets

PARTICULATE DETECTING SENSOR EMPLOYING PARALLEL LIGHT

BACKGROUND OF THE INVENTION

1. Field of the Invention

The present invention relates to a particulate detecting sensor for detecting particulate such as dust contained in smoke generated from a fire or in air. More particularly, this invention is concerned with a photoelectric particulate detecting sensor for detecting the presence of particulate by detecting scattered light occurring due to the particulate.

2. Description of the Related Art

In general, a particulate detecting sensor such as a high-sensitivity smoke sensor or dust monitor irradiates a light beam from a light source to a detection area, detects scattered light occurring due to particulates existent in the detection area, and thus detects the presence of the particulates. A light-emitting diode (LED), semiconductor laser (LD), xenon lamp, or the like is used as the light source. Scattered light occurring due to particulates is so weak that it is necessary for reliable detection of particulate to use a light source capable of supplying a large quantity of light.

However, many light sources capable of supplying a large quantity of light are generally characterized by a large quantity of heat generation and a great temperature dependence. There is a possibility that when temperature rises, a desired light-emission characteristic cannot be exerted.

A light beam emitted from a light source is spread conically or converged on a spot, and then projects into a detection area. Using a conically-spread light beam, a wide detection area can be set. However, since the light is radiated widely, it is reflected on the surface of an inner wall or the like in the detection area. Even when no particulate exists in the detection area, light referred to as stray light that is not scattered light is therefore readily detected by a light receiver. For constructing an optical system having a high signal-to-noise ratio, a large space is required for processing stray light. This results in enlarging the size of the particulate detecting sensor. On the other hand, when the spot convergence is adopted, a detection area is minimized although an optical system offering a high signal-to-noise ratio can be constructed. This technique is therefore unsuitable for particulate detection of volumes of air.

As mentioned above, as far as the known particulate detecting sensor is concerned, when a conically-spread light beam is used, there arises a problem that a high signal-to-noise ratio cannot be attained unless the entire sensor is made large in size. When a light beam converged on a spot is used, there arises a problem that it becomes difficult to detect particulate in volumes of air.

In the known particulate detecting sensor, there is another problem that a desired light-emission characteristic cannot be attained because of a temperature rise occurring when a light source is driven, and eventually it becomes impossible to detect particulate reliably.

The present invention attempts to solve the foregoing problems. An object of the present invention is to provide a particulate detecting sensor capable of reliably detecting particulate in volumes of air at a high signal-to-noise ratio despite having a compact design.

SUMMARY OF THE INVENTION

A particulate detecting sensor in accordance with a first aspect of the present invention is a photoelectric particulate detecting sensor for detecting particulate such as dust contained in smoke stemming from a fire or in air, comprising a light emitting means, an optical device for converting light emanating from the light emitting means into parallel light or collimated light, and a light receiving means that has a fan-shaped field pattern spreading along the optical path of the parallel light converted by the optical device, and that detects the scattered light of the parallel light which occurs due to particulate existent in the field pattern.

A particulate detecting sensor in accordance with the second aspect of the present invention is a photoelectric particulate detecting sensor for detecting particulate such as dust contained in smoke stemming from a fire or in air, comprising a light emitting means, an optical device for converting light emanating from the light emitting means into parallel light, a light receiving means for detecting the scattered light of the parallel light which occurs due to particulate existent in the optical path of the parallel light converted by the optical device, and a light trapping unit having a sealed box-like structure that includes an opening through which the parallel light enters.

A particulate detecting sensor in accordance with a third aspect of the present invention is a particulate detecting sensor for detecting smoke or particulate such as dust in sucked air, comprising: a casing that has an optical chamber defined inside thereof, includes an air inlet through which air is taken from the outside of the sensor into the optical chamber and an air outlet through which air is allowed to flow out from the optical chamber to the outside of the sensor, and thus forms a passage of air sucked into the optical chamber; a light emitting device located in the vicinity of the air passage within the optical chamber; and a light receiving device for detecting the scattered light of light emanating from the light emitting device which occurs due to particulate in the air.

DESCRIPTION OF THE PREFERRED EMBODIMENTS

Embodiments of the present invention will be described in conjunction with the appended drawings.

First Embodiment

Figure 1:
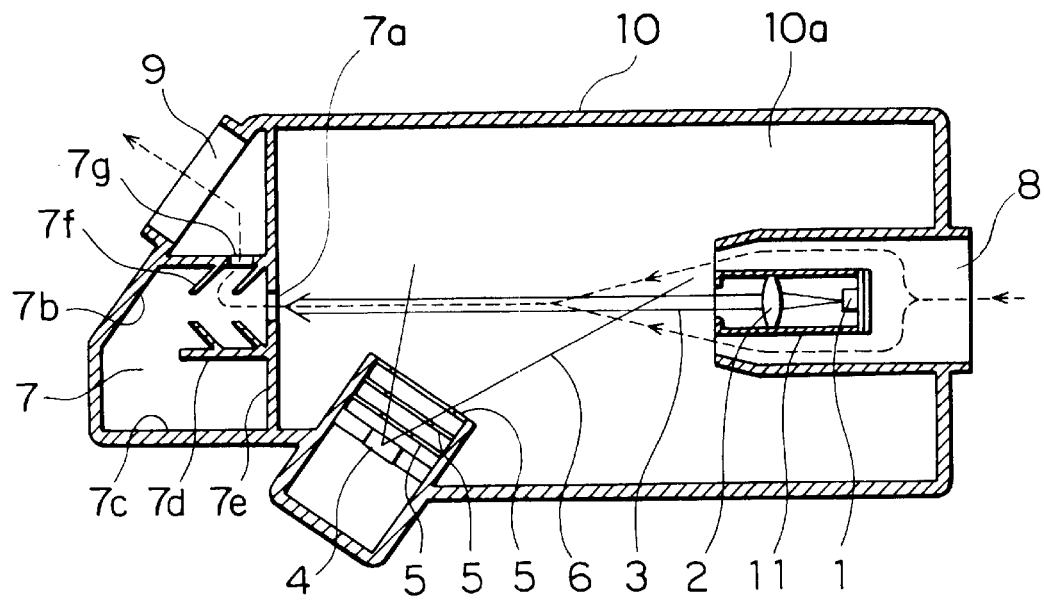
FIG. 1 is a side sectional view showing a particulate detecting sensor in accordance with the first embodiment of the present invention.
Figure 2:
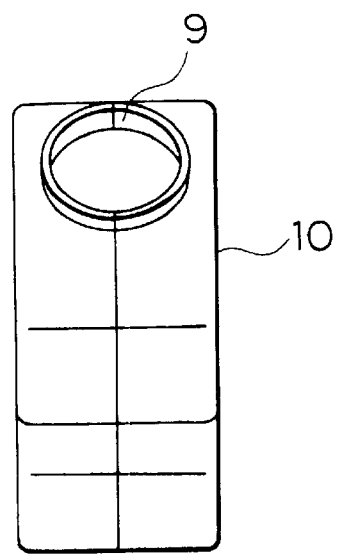
FIG. 2 is a front view showing the particulate detecting sensor of the first embodiment.

FIGS. 1 and 2 are a sectional view and front view of a particulate detecting sensor in accordance with the first embodiment of the present invention. An optical chamber 10a is defined inside a casing 10. An inlet 8, through which flows air or the like from a room that is an object of particulate detection, is formed at one end of the casing 10. A light emitting element 1 is placed inside the inlet 8, and a lens 2 is located in front of the light emitting element 1. A semiconductor laser (LD), light-emitting diode (LED), or the like can be used as the light emitting element 1. The lens 2 acts as an optical element for converting light emitted from the light emitting element 1 into collimated light or parallel light 3. The lens 2 can also be a single lens such as an aspheric lens. When a lens assembly is used as the lens 2, high-precision parallel light 3 can be formed. By inserting an optical diaphragm (pin hole) in front of the lens, light with little flare can be produced. The light emitting element 1 and lens 2 are encapsulated in, for example, a bottomed cylindrical holder 11 having an opening, through which the parallel light 3 passes, formed on the forward or front side thereof. The holder 11 is supported by a plurality of columns, which are not shown, within a cylindrical passage extending internally into casing 10.

Figure 3:
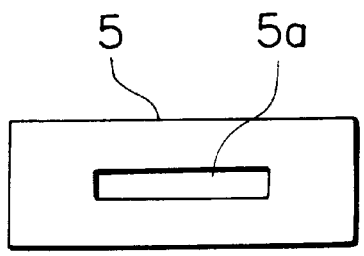
FIG. 3 is a front view showing an optical diaphragm employed in the first embodiment.

A light receiving element 4 is placed at a position spaced from the optical path of the parallel light 3 to ensure that the parallel light 3 does not enter element 4 directly. The light receiving element 4 is oriented in a direction having a given angle with respect to the optical path of the parallel light 3. A plurality of optical diaphragms 5 are arranged in front of the light receiving element 4. Each of the optical diaphragms 5 has, as shown in FIG. 3, an elongated rectangular opening 5a and is located so that the longitudinal direction of the opening 5a will be parallel to the sheet of paper containing FIG. 1. The opening 5a of the optical diaphragm 5 located farthest away from the light receiving element 4 has the largest length, and the opening 5a of the optical diaphragm 5 located closest to the light receiving element 4 has the smallest length. The widths of the openings 5a of all the optical diaphragms 5 are set to a certain value. The light receiving element 4 thus has a fan-shaped field pattern (field of view) 6 that, unlike a known conical field pattern, spreads along the optical path of the parallel light 3 and that has the same width as the openings 5a of the optical diaphragms 5. The smaller are the widths of the openings 5a, the more stray light can be prevented from entering the light receiving element 4. The widths are set to an appropriate value according to the size of parallel light emanating from the light emitting element 1.

A light trapping unit 7 is formed at the other end of the casing 10 and opposed to the light emitting element 1 and lens 2. The light trapping unit 7 has a substantially sealed box-like structure but has an opening 7a located on the optical path of the parallel light 3. The size of the opening 7a is slightly larger than the cross section of the parallel light 3 and is set to a value not allowing the parallel light 3 to impinge on the perimeter of the opening 7a. First to fourth reflection planar surfaces or planes 7b to 7e having low reflectances are formed inside the light trapping unit 7. The first reflection plane 7b is or inclined with respect to the optical path of the parallel light 3 so that the parallel light 3 entering through the opening 7a will be reflected toward the second reflection plane 7c. The second reflection plane 7c and third reflection plane 7d ara parallel to each other. The fourth reflection plane 7e connects the ends of the second and third reflection planes 7c and 7d to each other so as to block the optical path. A plurality of fins 7f are interposed between the opening 7a and first reflection plane 7b and are arranged along the periphery of the optical path of the parallel light 3 entering through the opening 7a.

A passage of air taken in through the inlet 8 is formed over the outer circumferences of the light emitting element 1 and lens 2 that are placed inside the inlet 8. A vent 7g of air is formed in a wall between adjoining fins 7f in the light trapping unit 7. An outlet 9 communicating with the vent 7g is formed at the other end of the casing 10. When a suction unit or the like that is not shown is used to suck air from a room and allow the air to flow in through the inlet 8, the air passes, as indicated with a broken line in FIG. 1, along the passage formed over the outer circumferences of the light emitting element 1 and lens 2, flows throughout the casing 10, enters the light trapping unit 7 through the opening 7a, and then flows out to the outside of the particulate detecting sensor through the vent 7g and outlet 9.

The air inlet 8 and air outlet 9 of the casing 10 are arranged at positions permitting an airflow to sufficiently pass through the field of view of the light receiving element 4.

Next, the operation of the particulate detecting sensor in accordance with the first embodiment will be described. First, given power is, for example, periodically supplied from a power supply that is not shown to the light emitting element 1 so that the light emitting element 1 will produce light intermittently. Light emitted from the light emitting element 1 passes through the lens 2 to become parallel light 3, and travels rectilinearly toward the opening 7a of the light trapping unit 7. At this time, since the parallel light 3 is produced by the lens 2, reflected light that occurs due to the inner wall or the like of the casing, 10 and causes stray light hardly enters the light receiving element 4. The parallel light 3 passing through a field pattern 6 of the light receiving element 4 enters the light trapping unit 7 through the opening 7a.

Figure 4:
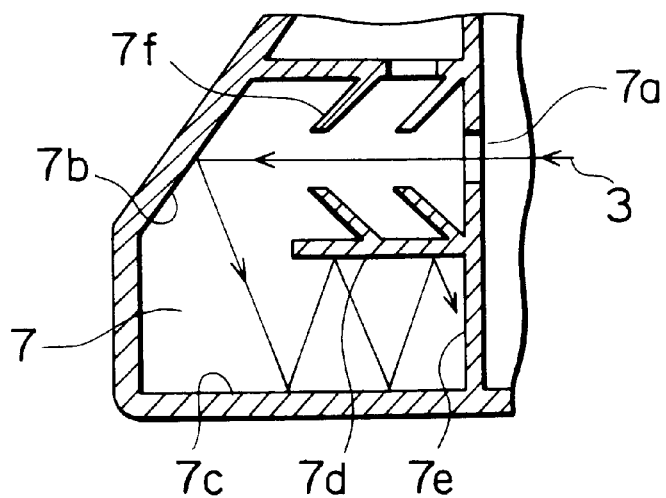
FIG. 4 shows an optical path to illustrate the operation of a light trapping unit in the first embodiment.

As shown in FIG. 4, the parallel light 3 passing through the opening 7a reaches the first reflection plane 7b of the light trapping unit 7. After being reflected toward the second reflection plane 7c because of the angle of the plane 7b, the whole light is further reflected from the second reflection plane 7c toward the third reflection plane 7d. The spacing between the end of the third reflection plane 7d and the first reflection plane 7b can be set to a value equivalent to the size of the opening 7a as long as the parallel light 3 is perfectly parallel light. However, since there is a possibility that light may be slightly spread or converged in the course of manufacturing an optical system, the spacing must be wide enough to pass light depending upon fluctuation in quality of the product and must permit the whole light reflected by the second reflection plane 7c to reach the third reflection plane 7d. The light reflected by the third reflection plane 7d is then repeatedly reflected by the second reflection plane 7c and third reflection plane 7d that have a positional relationship of their being parallel to each other, and then reaches the fourth reflection plane 7e. The reflection planes 7b to 7e are formed as planes of low reflectances. As the number of reflections increases, reflected light gradually attenuates in quantity.

The light reflected by the fourth reflection plane 7e goes back while repeatedly being reflected by the second reflection plane 7c and third reflection plane 7d. However, since the main light beam will not be reflected by a plane orthogonal to the beam in the light trapping unit 7, the light beam will not trace back the same optical path to a light emitting point. If the second reflection plane 7c and third reflection plane 7d did not have a positional relationship of being parallel to each other, the number of reflections made between them would decrease. This leads to a decrease in quantity of attenuating light. It is therefore preferred that the second reflection plane 7c and third reflection plane 7d be parallel to each other.

As mentioned above, while light is being reflected by the reflection planes in the light trapping unit 7, light decays in quantity. Nevertheless, some light still attempts to return to the opening 7a while being repeatedly reflected. The majority of the light is reflected by the plurality of fins 7f, returns into the light trapping unit 7, and then attenuates. If some light were not intercepted by the fins 7f but passed through the opening 7a to emerge from the light trapping unit 7, the light would be confined to the direction toward the light emitting element 1 and lens 2 owing to the operation of the plurality of fins 7f, and would not enter the light receiving element 4. An output signal sent from the light receiving element 4 in a state in which no particulate exists in the casing 10 is very small. Since the vent 7g communicating with the outlet 9 is formed in the light trapping unit 7, even if external light enters the particulate detecting sensor through the outlet 9, the external light decays in the light trapping unit 7 in the same manner as does the above parallel light 3. The external light will therefore not affect detection of particulate. This means that stray light can be reduced and detection can be achieved at a high signal-to-noise ratio.

When air or the like in a room that is an object of particulate detection is sucked using a suction unit or the like, which is not shown, in the above state, the air passes through the passage formed on the outer circumferences of the light emitting element 1 and lens 2 from the back end of the holder 11 toward the front end thereof, and then flows toward the opening 7a of the light trapping unit 7. In short, the air flows along the optical path of the parallel light 3. At this time, the scattered light of the parallel light 3 occurs due to particulate contained in an airflow. The scattered light is caught by the light receiving element 4. The light receiving element 4 then provides a detection output.

As mentioned above, when the light emitting element 1 emits parallel light 3, if the inlet 8 is formed in the vicinity of the light emitting element 1 and the outlet 9 is formed in the vicinity of an extension of the advance direction of the parallel light 3, that is, an extension of the optical path (optical axis) of the parallel light 3, a passage of air can be formed about the parallel light 3. Thus, the optical path and air passage can overlap one another. Consequently, light is irradiated to the passage of air by the light emitting element 1. Smoke can be routed reliably to the field pattern 6 that is a detection area. It can be prevented that the inner wall of the casing 10 is soiled by an airflow. Since the inlet 8 is located behind the light emitting element 1, the lens 2 in the holder 11 will not be soiled.

The light receiving element 4 has the fan-shaped field pattern 6 that spreads along the optical path of the parallel light 3 owing to the plurality of optical diaphragms 5. The light receiving element 4 can therefore effectively detect scattered light occurring in a wide range along the optical path of the parallel light 3, and obtain a high light-reception intensity. This makes it possible to widen the field pattern 6 of the light receiving element 4 in fan shape, in other words, the angle of view of the light receiving element 4 can be enlarged because little stray light exists due to the use of the parallel light 3. Since particulate can be detected in a wide detection area extending along the optical path of the parallel light 3, the particulate detecting sensor can perform particulate detection on volumes of air simultaneously at a high signal-to-noise ratio despite the compact design.

Since the holder 11 accommodating the light emitting element 1 and lens 2 is placed in a passage of sucked air, the light emitting element 1 is forcibly and automatically cooled by an airflow via the holder 11. Even if a device featuring a large quantity of heat generation or a high temperature dependence, such as a semiconductor laser, is used as the light emitting element 1, the light emitting element 1 can be driven satisfactorily.

When the columns of the holder 11 are shaped like thin blades and made of a material with a high heat radiation ability, the heat radiation effect improves. The columns determine a volume of air to be sucked, that is, a flow rate.

Second Embodiment

Figure 5:
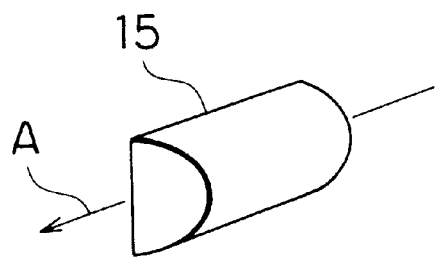
FIG. 5 is a perspective view showing a cylindrical lens employed in a particulate detecting sensor in accordance with the second embodiment.

Instead of the plurality of optical diaphragms 5 employed in the first embodiment, a cylindrical lens 15 shown in FIG. 5 may be placed in front of the light receiving element 4. The cylindrical lens 15 is placed so that the cylindrical axis A of the cylindrical lens 15 will be perpendicular to the sheet of paper containing FIG. 1, whereby the fan-shaped field pattern 6 can be formed in the same manner as that is in the first embodiment. Since only one cylindrical lens 15 is sufficient, a simple structure ensues. The optical diaphragms 5 each having the rectangular opening such as the one shown in FIG. 3 may be used in combination with the cylindrical lens 15.

Third Embodiment

Figure 6:
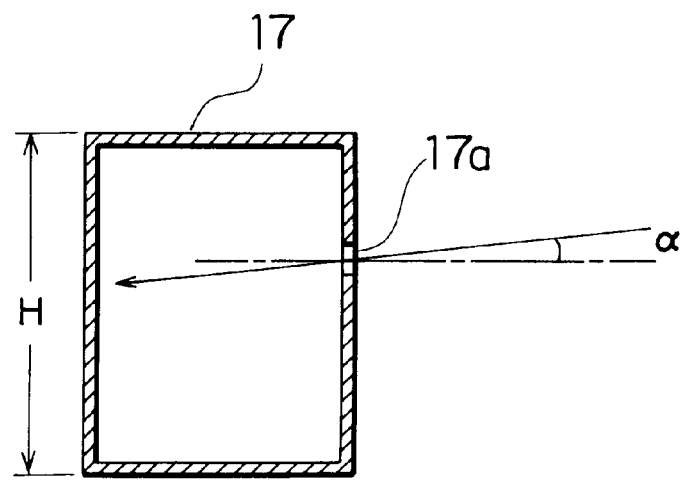
FIG. 6 is a sectional view schematically showing a light trapping unit employed in a particulate detecting sensor in accordance with the third embodiment.

In the first embodiment, the parallel light 3 enters the light trapping unit 7 through the opening 7a at a right angle. As shown in FIG. 6, the particulate detecting sensor may have a structure such that the parallel light 3 enters a light trapping unit 17 through an opening 17a in a direction slanted or inclined by an angle α with respect to a direction right-angled to the opening 17a. This embodiment substantially extends the distance between reflection planes in the light trapping unit 17, and reduces the quantity of light returning through the opening 17a. This effect is intensified with an increase in height H of the light trapping unit 17. In the light trapping unit 17, a plurality of reflection planes are formed in the same manner as those in the light trapping unit 7 of the first embodiment. The reflection planes are omitted in FIG. 6.

Fourth Embodiment

Figure 7:
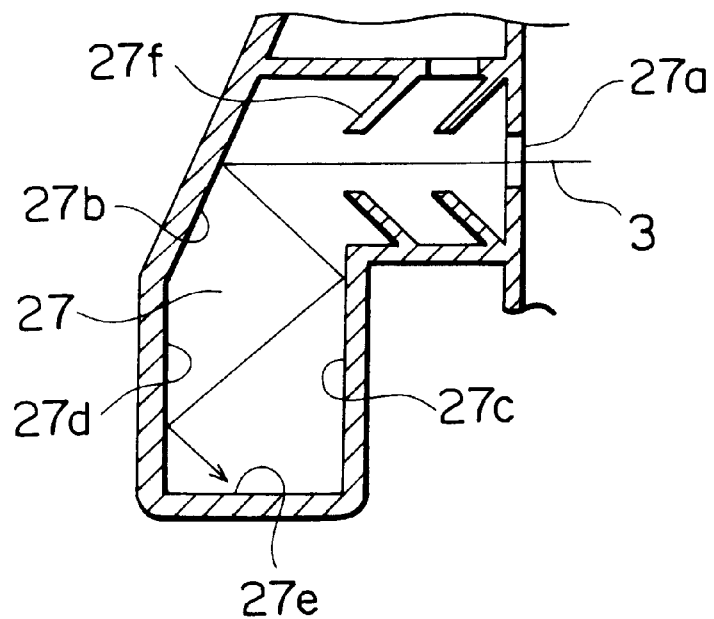
FIG. 7 is a sectional view showing a light trapping unit employed in a particulate detecting sensor in accordance with the fourth embodiment.

In the light trapping unit 7 of the first embodiment shown in FIG. 4, the mutually-parallel second and third reflection planes 7c and 7d are formed at positions at which the reflection planes can be parallel to the parallel light 3 entering through the opening 7a. As is apparent from a light trapping unit 27 shown in FIG. 7, mutually-parallel second and third reflection planes 27c and 27d may be located perpendicularly to the parallel light 3 entering through an opening 27a. The third reflection plane 27d adjoins a first reflection plane 27b. A fourth reflection plane 27e connects the ends of the second and third reflection planes 27c and 27d to each other so as to block an optical path. A plurality of fins 27f are interposed between the opening 27a and first reflection plane 27b. Even this structure exerts the same effect as the light trapping unit 7 of the first embodiment. Depending on the structure of an entire particulate detecting sensor, either of the light trapping units shown in FIGS. 4 and 7 may be selected.

Fifth Embodiment

Figure 8:
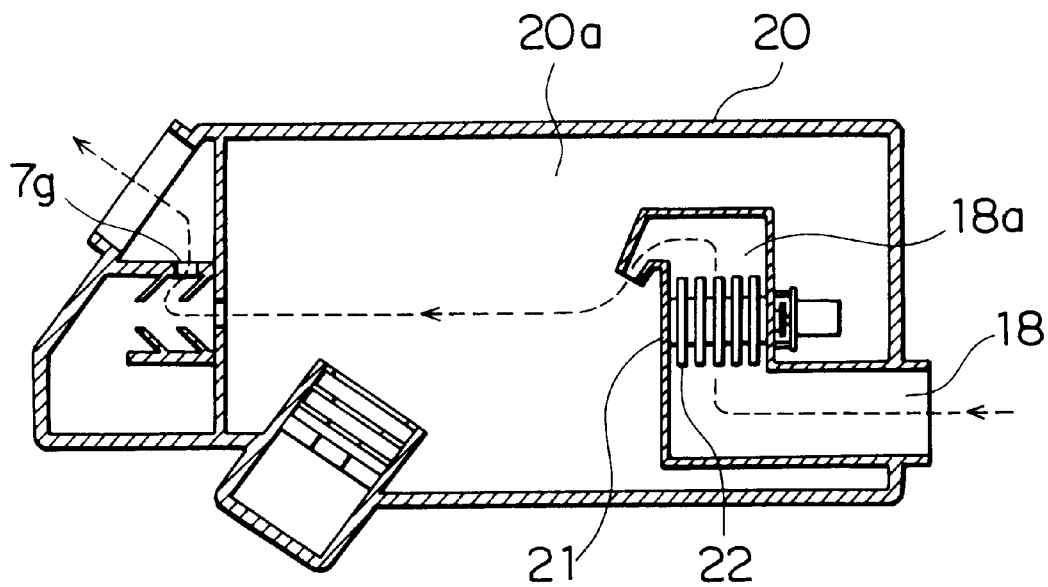
FIG. 8 is a side sectional view showing a particulate detecting sensor in accordance with the fifth embodiment.
Figure 9:
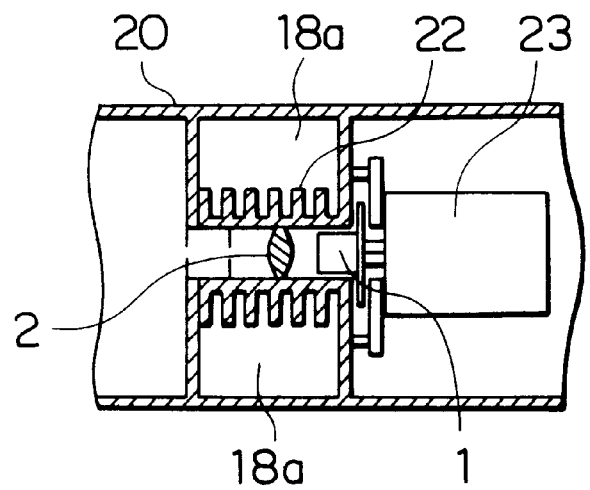
FIG. 9 is a plan sectional view showing a cross section of a light emitting unit for the particulate detecting sensor in accordance with the fifth embodiment.

In the first embodiment, an airflow is produced to flow from the back end of the cylindrical holder 11 accommodating the light emitting element 1 and lens 2 toward the front end thereof. As shown in FIG. 8, a cylindrical passage 18a may be formed so as to protrude inwardly from inlet 18 so that air sucked through an inlet 18 can flow in a direction right-angled to a cylindrical light emitting unit 21. A plurality of cooling fins 22 are formed over the outer circumference of the light emitting unit 21 in parallel to a flow of air in the passage 18a. Since the light emitting unit 21 penetrates the passage 18a in a right-angled direction, as shown in FIG. 9, the passage 18a is divided into portions lying on both sides of the light emitting unit 21. The light emitting element 1 and lens 2 are incorporated in the light emitting unit 21. A drive circuit 23 is connected to the light emitting element 1.

Owing to the foregoing structure, air sucked through the inlet 18 effectively comes into contact with the cooling fins 22 formed in parallel with the flow of air so as to forcibly and automatically cool down the light emitting unit 21. Thereafter, the air is introduced from near the distal end of the light emitting unit 21 into an optical chamber 20a. This causes the cooling efficiency for the light emitting unit 21 and eventually for the light emitting element 1 to improve. Even when a device featuring a large quantity of heat generation or a high temperature dependence, such as a semiconductor laser, is used as the light emitting element 1, the light emitting element 1 can be driven satisfactorily.

Sixth Embodiment

Figure 10A:
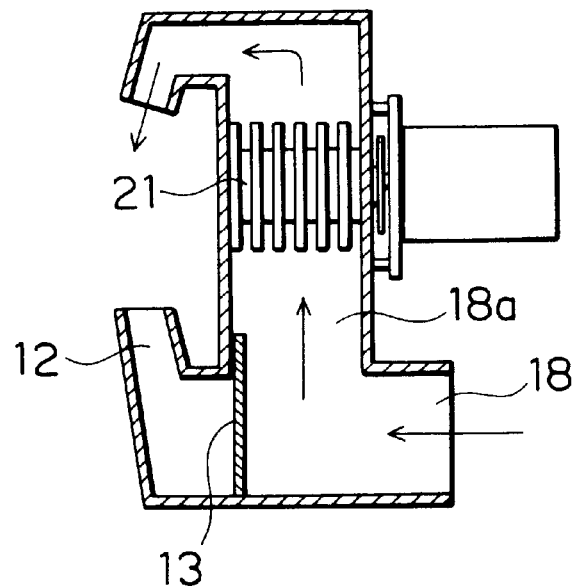
FIGS. 10A and 10B are side sectional views showing a normal state and a state thereof in which a hot airflow is introduced of an air introducing unit employed in a particulate detecting sensor in accordance with the sixth embodiment, respectively.
Figure 10B:
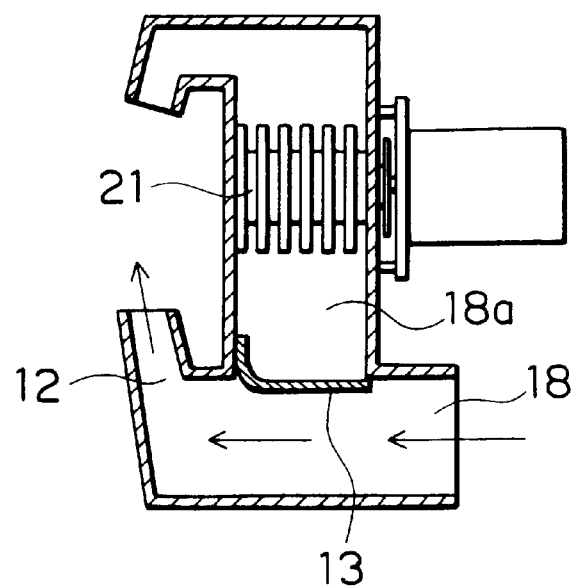

In the particulate detecting sensor of the fifth embodiment, as shown in FIG. 10A, a bypass 12 of air may be formed in an air introducing unit for taking in air from the outside into the sensor, and a cutoff means 13 for restricting the flow of air may be interposed between the passage 18a and bypass 12. The cutoff means 13 is made of a known shape memory material. At a normal temperature, as shown in FIG. 10A, the cutoff means 13 is in a stretching state so as to cut off the communication between the inlet 18 and bypass 12 and to allow the inlet 18 to communicate with the passage 18a. At a high temperature exceeding a given temperature, as shown in FIG. 10B, the cutoff means 13 bends to cut off the communication between the inlet 18 and passage 18a and to allow the inlet 18 to communicate with the bypass 12.

Owing to the employment of the cutoff means 13, in a normal state, air taken in through the inlet 18 can be allowed to flow along the passage 18a in order to cool down the light emitting unit 21. When a high-temperature hot airflow flows in through the inlet 18 because of occurrence of a fire or the like, the cutoff means 13 can bend to introduce the hot airflow into the optical chamber 20a via the bypass 12. Thus, it can prevent the light emitting unit 21 from being heated due to the hot airflow. Moreover, smoke or the like can be detected using the air introduced via the bypass 12.

Seventh Embodiment

Figure 11:
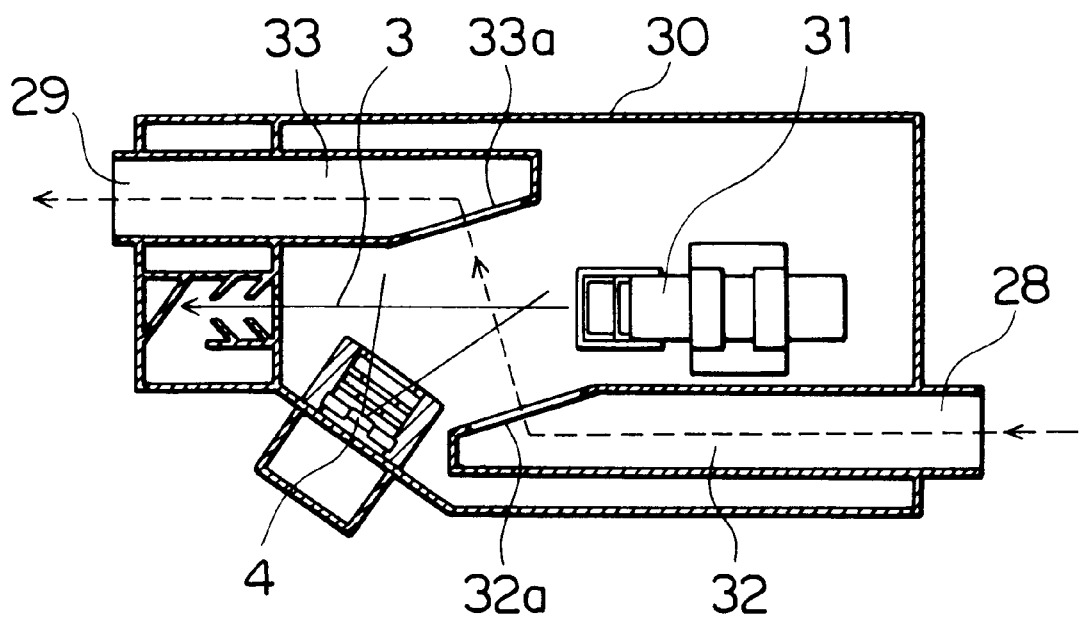
FIG. 11 is a side sectional view showing a particulate detecting sensor in accordance with the seventh embodiment.

In the aforesaid embodiments, air is introduced from near the light emitting element 1 into the casing 10 or 20, and the vent 7g for air is formed in the light trapping unit 7. Thus, an airflow indicated with a broken line in an associated drawing is produced along the optical path of the parallel light 3 emanating from the light emitting element 1. As shown in FIG. 11, a passage may be formed so that an airflow will intersect the optical path of the parallel light 3 in a detection area of the light receiving element 4. A take-in duct 32 and take-out duct 33 both of which are cylindrical are connected to an inlet 28 and outlet 29 of a casing 30. Openings 32a and 33a each of which is shaped like an elongated slit and through which air flows are formed at the distal ends of the take-in duct 32 and take-out duct 33. The openings 32a and 33a are parallel to each other and opposed to each other with the optical path of the parallel light 3 emanating from a light emitting unit 31 between them. The optical path and passage of air meet not at a point but linearly. Sucked air flows from the inlet 28 to the outlet 29 along the passage indicated with a broken line in FIG. 11. In the detection area of the light receiving element 4, the air flows askew relative to the optical path of the parallel light 3. Even this structure enables the light receiving element 4 to detect scattered light occurring due to particulate in the air. The slit-like openings 32a and 33a are used to attain an airflow with a cross section in a slit pattern. This is to increase the height of the smoke passage for the purpose of avoiding a pressure loss due to decrease of the cross-sectional area of the passage.

Alternatively, an inlet and outlet that are each shaped like an elongated slit may be formed at positions at which a plane containing the optical path of parallel light emitted from a light emitting device intersects a casing. For example, in FIG. 11, the take-in duct 32 is parallel to the sheet of paper containing FIG. 11. Alternatively, a take-in duct may be mounted on each of the right-hand and left-hand outer walls of the casing 30 so that a passage of sucked air can be formed perpendicularly to the sheet of paper containing FIG. 11. This alternative can also introduce the sucked air to parallel light and therefore detect smoke reliably.

Structures in which a light emitting element is placed in the vicinity of an inlet have been described so far. Alternatively, a light emitting element may be placed in the vicinity of an outlet of air, and the inlet of air may be located on an extension of the optical path of light emitted from the light emitting element.

What is claimed is:

1. A photoelectric particulate detecting sensor for detecting particulate in smoke stemming from a fire or in air, said sensor comprising:

a casing having therein an air inlet and an air outlet defining an airflow passage for air to flow from said air inlet toward said air outlet through said casing, said casing being closed other than for said air inlet and said air outlet;

a light emitting means housed by said casing and positioned in an air introduction area and in a position adjacent said air inlet;

an optical element housed by said casing for converting light emitted from said light emitting means into parallel light along an optical path within said casing;

a light receiving means, housed by said casing, for defining a field pattern spreading along said optical path and thereby for detecting scattered light of said parallel light which occurs due to particulate existent in said airflow passage at said field pattern; and said airflow passage between said air inlet and said air outlet extending linearly with said optical path of light emitted from said light emitting means.

2. A sensor according to claim 1, wherein said light emitting means is positioned in the vicinity of said airflow passage from said air inlet toward said air outlet.

3. A sensor according to claim 2, wherein said light emitting means is positioned in an air introduction cylinder extending from said air inlet into the inside of said casing.

4. A sensor according to claim 2, wherein one of said air inlet and said air outlet is positioned in the vicinity of said light emitting means while the other of said air inlet and said air outlet is positioned in the vicinity of an extension of said optical path, and said light emitting means irradiates light to said airflow passage.

5. A sensor according to claim 2, further comprising a holder positioned in said airflow passage, said holder being shaped like a cylinder having an open front side, and said light emitting means being positioned inside said holder.

6. A sensor according to claim 5, wherein said holder has cooling fins on an outer circumference thereof.

7. A sensor according to claim 2, further comprising a cutoff means for cutting off a flow of air to adjacent said light emitting-means when a hot airflow flows in through said air inlet.

8. A sensor according to claim 7, wherein when a hot airflow flows in through said air inlet, said cutoff means introduces the hot airflow into said casing via a bypass ahead of said light emitting means.

9. A sensor according to claim 2, wherein said air inlet and said air outlet are opposed to each other with said optical path therebetween, said air inlet and said air outlet are shaped as mutually-parallel slits, and said airflow passage between said air inlet and said air outlet extends linearly with said optical path.

10. A sensor according to claim 1, wherein said air inlet and said air outlet are each shaped like a slit, and said airflow passage between said air inlet and said air outlet extends linearly with said optical path of light emitted from said light emitting means.

11. A sensor according to claim 1, further comprising a light trapping unit positioned in front of said light emitting means and operable to prevent parallel light, which has passed through said field pattern of said light receiving means, from entering said light receiving means.

12. A sensor according to claim 11, wherein one of said air inlet and said air outlet is formed in said light trapping unit.

13. A sensor according to claim 11, wherein said light trapping unit comprises a sealed box-like structure including an opening through which enters parallel light having passed through said field pattern of said light receiving means, a first reflection plane for receiving said parallel light, second and third reflection planes which are parallel to each other, and a fourth reflection plane for connecting said second and third reflection planes to each other and blocking an optical path, said parallel light that has entered through said opening and been reflected by said first reflection plane to said second reflection plane gradually decaying while being repeatedly reflected by said second reflection plane and said third reflection plane.

14. A sensor according to claim 13, wherein said light trapping unit includes a plurality of fins located behind said opening and arranged in a periphery of said optical path of parallel light entering through said opening.

15. A sensor according to claim 1, wherein said light receiving means includes a light receiving element, and a plurality of optical diaphragms positioned in front of said light receiving element to form said field pattern.

16. A sensor according to claim 1, wherein said light receiving means includes a light receiving element, and a cylindrical lens positioned in front of said light receiving element to attain said field pattern.

17. A sensor according to claim 1, wherein said field pattern is fan-shaped.

18. A photoelectric particulate detecting sensor for detecting particulate in smoke stemming from a fire or in air, said sensor comprising:

a casing having therein an air inlet and air outlet defining an airflow passage for air to flow from said air inlet toward said air outlet through said casing, said casing being closed other than for said air inlet and said air outlet;

a light emitting means housed by said casing;

an optical element housed by said casing for converting light emitted from said light emitting means into parallel light along an optical path within said casing;

a light receiving means, housed by said casing, for defining a field pattern spreading along said optical path and thereby for detecting scattered light of said parallel light which occurs due to particulate existent in said airflow passage at said field pattern; and said air inlet and said air outlet being opposed to each other with said optical path therebetween, said air inlet and said air outlet being shaped as mutually-parallel slits, said airflow passage between said air inlet and said air outlet intersecting said optical path of light emitted from said light emitting means.

19. A sensor according to claim 18, further comprising a light trapping unit positioned in front of said light emitting means and operable to prevent parallel light, which has passed through said field pattern of said light receiving means, from entering said light receiving means.

20. A sensor according to claim 19, wherein said light trapping unit comprises a sealed box-like structure including an opening through which enters parallel light having passed through said field pattern of said light receiving means, a first reflection plane for receiving said parallel light, second and third reflection planes which are parallel to each other, and a fourth reflection plane for connecting said second and third reflection planes to each other and blocking an optical path, said parallel light that has entered through said opening and been reflected by said first reflection plane to said second reflection plane gradually decaying while being repeatedly reflected by said second reflection plane and said third reflection plane.

21. A sensor according to claim 20, wherein said light trapping unit includes a plurality of fins located behind said opening and arranged in a periphery of said optical path of parallel light entering through said opening.

22. A sensor according to claim 18, wherein said light receiving means includes a light receiving element, and a plurality of optical diaphragms positioned in front of said light receiving element to form said field pattern.

23. A sensor according to claim 18, wherein said light receiving means includes a light receiving element, and a cylindrical lens positioned in front of said light receiving element to attain said field pattern.

24. A sensor according to claim 18, wherein said field pattern is fan-shaped.

* * * * *